United States Patent [19]

Shasha

[11] 4,382,813

[45] May 10, 1983

[54] ENCAPSULATION BY ENTRAPMENT WITHIN STARCH ADDUCT MATRIX

[75] Inventor: Baruch S. Shasha, Peoria, Ill.

[73] Assignee: The United States of America as represented by the Secretary of Agriculture, Washington, D.C.

[21] Appl. No.: 202,396

[22] Filed: Oct. 30, 1980

[51] Int. Cl.$^3$ .................. A01N 43/00; A01N 25/28; A61K 9/26; B01J 13/02

[52] U.S. Cl. ........................................ 71/88; 71/64.11; 71/100; 71/105; 71/117; 71/118; 71/121; 71/122; 71/DIG. 1; 424/22; 424/35; 264/4.3; 427/213.32

[58] Field of Search ................... 252/316; 424/35, 22; 536/45, 47; 71/88, 100, 117, DIG. 1, 64.11

[56] References Cited

U.S. PATENT DOCUMENTS

| | | | |
|---|---|---|---|
| 2,588,463 | 3/1952 | Balassa | 536/47 X |
| 3,786,123 | 1/1974 | Katzen | 424/35 X |
| 4,277,364 | 7/1981 | Shasha et al. | 252/316 |

FOREIGN PATENT DOCUMENTS

| | | | |
|---|---|---|---|
| 1163023 | 9/1969 | United Kingdom | 252/316 |

OTHER PUBLICATIONS

W. J. Connick, Jr., "Encapsulation of Herbicides in Alginate Gels for Aquatic Weed Control," Proceedings of 6th International Symposium on Controlled Release of Bioactive Materials, New Orleans, LA, Aug. 6-8, 1979.

*Primary Examiner*—Richard D. Lovering
*Attorney, Agent, or Firm*—M. Howard Silverstein; David G. McConnell; Curtis P. Ribando

[57] ABSTRACT

Water-insoluble chemical biological agents to be encapsulated are dispersed in an aqueous paste of a starch-containing material alkoxide. Subsequent addition of selected water-soluble alkali earth metal cations insolubilize the paste, thereby entrapping the agents in a protective matrix. Encapsulation of biologically active compositions provides a shield against hostile environments, improves safety in handling, and slows the release of such compounds to the surrounding medium. Highly volatile liquids are protected against losses by evaporation. Encapsulation also provides protection against decomposition from exposure to ultraviolet light.

11 Claims, No Drawings

ENCAPSULATION BY ENTRAPMENT WITHIN STARCH ADDUCT MATRIX

CROSS REFERENCE TO RELATED APPLICATIONS

This application is related to commonly assigned application Ser. No. 202,395, filed concurrently herewith, now U.S. Pat. No. 4,348,492, by Baruch S. Shasha and Thomas P. Abbott entitled "Starch Adduct Encasement of Particulate Elastomers".

BACKGROUND OF THE INVENTION

1. Field of the Invention

This invention relates to a method of encapsulating chemical biological materials in a matrix of water-insoluble starch-based adducts, and to the compositions prepared thereby.

2. Description of the Prior Art

Prior art methods of encapsulation can be described in two major categories, physicomechanical and chemical. Physicomechanical techniques include the following: spray drying; dipping or centrifuging technique; multiple nozzle spraying; fluidized bed coating; electrostatic microencapsulation; and vacuum encapsulation. The most important chemical encapsulation techniques include simple and complex coacervation and interfacial polymerization, the latter of which encompasses the prior art most relevant to the instant invention. The interfacial polymerization method necessitates the use of at least a two-phase system. One of the reactants must be soluble in the continuous phase and insoluble in the discontinuous phase (core material). The other reactant must be insoluble in the continuous phase and soluble in the discontinuous phase. The polymerization reaction occurs at the interface between the two phases forming a polymer shell around the core material, thereby completely enveloping it. This shell must be insoluble in both phases. In this method either phase can be an aqueous system. See U.S. Pat. Nos. 3,577,515 and 3,575,882 and British Pat. No. 1,163,023.

The above-mentioned encapsulation methods are multistep processes which require carefully controlled conditions or special equipment. They are time consuming and expensive, often requiring elevated temperatures and pressures other than ambient; and they all require at least a two-phase system. Many require expensive, toxic, and flammable solvents which must be recovered. Coacervation is limited to the encapsulation of oils in materials which have the capacity to form gels. Interfacial polymerization techniques, also requiring two or more phases, are limited essentially to expensive synthetic polymerization systems, many of which are petrochemicals and which generally produce nonbiodegradable polymers. To make these systems more economical and to prevent ecological contamination, unreacted monomers must be recovered. The only system that appears to be useful for coating solid particles is the fluidized bed technique.

An alternative to the conventional interfacial polymerization methods is the film-forming system as taught in Connick [Proc. of the 6th International Symp. on Controlled Release of Bioactive Materials, pp. III-1 to III-3 (Aug. 6-8, 1979)]. In accordance with this method, the active ingredient dispersed in an aqueous solution of about 1% sodium alginate is added dropwise to a gellant bath consisting of a metal salt such as calcium chloride to form small gel spheres. While this procedure is applicable to the encapsulation of a wider variety of chemical substances and formulations than interfacial polymerization, it is inherently slow, it does not lend itself to the incorporation of high concentrations of active ingredient, and the product is not easily recovered from the gellant bath.

In copending applications Ser. No. 733,968, filed Oct. 19, 1976, now U.S. Pat. No. 4,277,364, and Ser. No. 150,550, filed May 16, 1980, now U.S. Pat. No. 4,344,857, disclose methods of encapsulation whereby a polyhydroxy polymer xanthate and a coupling agent are reacted from a single phase to form an insolubilized matrix, thereby entrapping the chemical biological agent. The Shasha et al. system has the advantage of operating in both aqueous and nonaqueous two-phase systems, as well as in single-phase systems in which the matrix-forming materials and the core material are soluble in the same solvent. Another advantage is that the entire reaction mixture is converted into a solidified mass which is readily dried and ground into a usable product after pressing out excess water. This obviates the recovery from a liquid medium as necesssitated by most coacervation and interfacial polymerization methods. However, widespread commercial acceptance of the Shasha et al. methods has been hindered by the reluctance of the industry to handle carbon disulfide which is flammable and toxic.

SUMMARY OF THE INVENTION

I have now unexpectedly discovered a method of encapsulating water-insoluble, chemical biological agents in which the matrix material forms a readily recoverable solidified mass surprisingly similar to that of Shasha et al., without the use of xanthates. The system is equally operative for dispersed liquids and solid particulate core materials which become entrapped by the rapid insolubilization of a starch-containing material (SCM) alkoxide with a suitable bivalent cation selected from the group consisting of calcium, barium, and strontium.

In accordance with this discovery, it is an object of the invention to provide a simple, industrially acceptable method for the encapsulation of core materials.

It is also an object of the invention that the primary matrix-forming material be derived from natural renewable, resources.

It is a further object of the invention to provide a novel product in which discontinuous domains of biologically active core material are entrapped by a continuous matrix of insolubilized starch-containing material.

Another object of the invention is to provide a product in which the encapsulated substance is sufficiently protected to be safe for handling, controllably released to the environment, and resistant to losses by volatilization and sunlight decomposition.

Other objects and advantages of this invention will become readily apparent from the ensuing description.

DETAILED DESCRIPTION OF THE INVENTION

The starch-containing materials (SCM) for use in accordance with the invention include the natural starches such as cereal, potato, and tapioca starch, and flours containing the same, as well as starch fractions (e.g., amylose and amylopectin), derivatized starches such as methyl starch and hydroxyethyl starch and modified starches. As a practical matter, these starches will be in their original granular form, though pregelatinized or partially gelatinized starch may also be used.

The SCM is prepared for the encapsulation reaction by conversion to an alkoxide with an alkali metal hydroxide. Sodium and potassium hydroxide are the most suitable reagents for this purpose and will react with the SCM in aqueous suspension at ambient temperature. The alkoxidation will simultaneously effect gelatinization provided that the alkali metal is provided at a level of at least about 1 mole per 2.5 moles of anhydroglucose units (AGU). As the molar ratio of alkali metal:AGU approaches 1:1, the extent of subsequent encapsulation is significantly reduced. The preferred range is between 1:2.5 and 1:2. The gelatinization and alkoxidation solubilize the starch to the extent possible for a polymer, thereby producing a paste in the presence of water. For purposes of this invention, the starch in paste form is considered to be in the aqueous phase which will constitute the continuous phase of the encapsulation system.

The concentration of SCM in the aqueous suspension prior to pasting should be maintained within the range of 6–20% solids. Below 6%, the active ingredient is not completely encapsulated. Above about 15%, the viscosity increases to a point of rendering the paste unworkable, though we have found that solids up to 20% can be employed if the paste is subjected to high shear, such as by treatment for a few seconds in a "Waring" blender. The preferred SCM concentration in regard to the extent of encapsulation and the general handling characteristics is in the range of 7–11% with 10% being about optimum.

The core material to be encapsulated is dispersed in the SCM paste by any conventional means of obtaining a relatively uniform distribution. The domains of agent which constitute the discontinuous phase of the dispersion should be sufficiently small so as to render the dispersion stable until the paste is insolubilized. It would be within the skill of a person in the art to determine the maximum level at which a particular agent can be effectively loaded into the system. However, based upon the studies with trifluralin as reported in the exampes below, it is clear that as much as 50% active ingredient based upon the dry weight of the starch can be incorporated into the dispersion with up to 95% encapsulation. For purposes of performances, effective amounts of core materials depend entirely on the type and characteristics of the core material, on matrix thickness, and on the intended utility of the product. A very volatile liquid, for instance, would require a thicker structure than a nonvolatile solid, and accordingly should be incorporated at a lower level. Similarly, a volatile liquid to be completely withheld from the environment would be incorporated at a lower level than one to be used as a slow-release pesticide. "An effective amount of a suitable biological agent" is defined herein as that amount of core material which will achieve the desired result (e.g., attract, repel, or kill pests, release a detectable aroma or flavor, or enhance the growth of plants) when the encapsulated composition containing the effective amount of the agent is placed in the proper environment.

Chemical biological agents which are suitable for encapsulation in accordance with this invention may be any organic or inorganic solids capable of being finely divided or any liquid, provided that the agent is water insoluble, does not interfere with the encapsulating process, and does not react with or dissolve the encapsulating matrix. Particularly envisioned are chemicals and chemcal formulations which meet the above criteria and which are classified as a known herbicide, insecticide, fungicide, nematocide, bacteriocide, rodenticide, molluscide, acaricide, larvacide, fumigant, animal repellant, insect repellant, plant growth regulator, fertilizer, pheromone, sex lure, flavor composition, or odor composition.

Exemplary herbicides include S-ethyl dipropylcarbamothioate, S-propyl dipropylcarbamothioate, S-propyl butylethylcarbamothioate, S-ethyl cyclohexylethylcarbamothioate, S-ethyl bis(2-methylpropyl)-carbamothioate, S-ethyl hexahydro-1-$\underline{H}$-azepine-1-carbothioate, S-(2,3,3,-trichloro-2-propenyl)bis(1-methylethyl)carbamothioate, 2,6-dinitro-N,N-dipropyl-4-(trifluoromethyl) benzenamine, N-butyl-N-ethyl-2,6-dinitro-4-(trifluoromethyl) benzenamine, N-(cyclopropylmethyl)-2,6-dinitro-N-propyl-4-(trifluoromethyl) benzenamine, 2-chloro-N-(2-ethyl-6-methylphenyl)-N-(2-methoxy-1-methylethyl) acetamide, 2-chloro-N-(2,6-diethylphenyl)-N-(methoxymethyl) acetamide, 2,4-dichlorophenoxyacetic acid, propylene glycol butyl ether, and 2,6-dichlorobenzonitrile.

Exemplary fungicides include 3a,4,7,7a-tetrahydro-2-[(trichloromethyl)thio]-1-$\underline{H}$-isoindole-1,3(2$\underline{H}$)-dione, and 3a,4,7,7a-tetrahydro-2-[(1,1,2,2-tetrachloroethyl)-thio]-1-$\underline{H}$-isoindole-1,3(2$\underline{H}$)-dione.

Exemplary insecticides include N-[[(4-chlorophenyl)amino] carbonyl]-2,6-difluorobenzamide, 1,1'-(2,2,2-trichloroethylidene) bis(4-chlorobenzene), O,O-diethyl O-6-methyl-2-(1-methylethyl)-4-pyrimidinyl phosphorothioate, and O -ethyl-S-phenyl ethylphosphonodithioate. 1,2-dibromo-3-chloropropane is illustrative of a suitable nematocide. Other compositions suitable as core materials for use in accordance with the invention will be known to those skilled in the art. Core materials dissolved in water-immiscible solvents and compatible combinations of the above types of compositions are also easily encapsulated by the instant method.

The SCM paste with the dispersed active ingredient is insolubilized by the addition of a source of bivalent cations selected from the group of calcium, barium, and strontium. The source must be readily ionizable in water and thereby able to react with the SCM alkoxide from a single phase. The cations displace the alkali metal ions on the alkoxide to produce an insoluble adduct. The cation source should be predissolved in an aqueous medium, and it should be rapidly mixed with the paste dispersion in order to effect a substantially instantaneous insolubilization. The result is the formation of a substantially homogeneous mass analogous to the precursive dispersion in which, now, discontinuous domains of active ingredient are more or less uniformly dispersed throughout the continuous, insolubilized SCM matrix.

The preferred sources for the bivalent cations are the chloride salts of the respective metals. Because of its high solubility, nontoxicity, and low cost, calcium chloride is the preferred insolubilizing agent. The molar ratio of bivalent cation:alkali metal should be greater than 1:2.5 in order to prevent the product from becoming gummy and difficult to isolate. Generally, the ratio of these two entities will be between 1:2 and 1:0.5.

Since the entire pot mixture (i.e., SCM paste, dispersed active ingredient, and cation source) is converted into a homogeneous mass, the recovery procedure does not require a separatory step, though it may be desirable to press out excess moisture prior to drying. The matrix is normally crumbled by the mixing action during insolubilization, and may be easily washed, filtered, dried, and further ground if necessary by any conventional methods. Loss of core material will be negligible provided that the washing is conducted with water or other solvent that does not dissolve or react with the matrix material.

After the product has dried to yield a friable granular or powdered material, rewetting initiates release of the active ingredient. Fields, gardens, and the like in which pesticides, attractants, repellants, plant growth regulators, and fertilizers are normally used contain sufficient natural or added moisture to initiate release. Odor and flavor compositions, which are used as foods, are released from the encapsulating matrix by moisture contained in or added to the food product. While not desiring to be bound to any particular theory, it is believed that the mechanism of release is effected by the biodegradation of the SCM matrix as well as by displacement by water and diffusion through imperfections in the matrix.

The following examples are intended only to further illustrate the invention and are not intended to limit the scope of the invention which is defined by the claims.

EXAMPLE 1

A. On a dry weight basis, 162 parts of unmodified pearl corn starch was suspended in 1000 parts of water and was gelatinized at room temperature by the addition of 40 parts sodium hydroxide in 300 parts water. The molar ratio of NaOH:starch AGU was 1:1, and the resultant sodium starchate paste has a starch concentration of 10.8%.

B. The procedure described in Example 1(A) above was repeated except that the gelatinization was carried out by the addition of 20 parts sodium hydroxide in 300 parts water. The molar ratio of NaOH:starch AGU was 1:2, and the resultant sodium starchate paste had an equivalent starch concentration of 10.9%.

EXAMPLE 2

Three hundred seventy parts sodium starchate paste as prepared in Example 1(B) was mixed with 1.3 parts of a melt of trifluralin herbicide [2,6-dinitro-N,N-dipropyl-4-(trifluoromethyl)benzenamine]. Ten parts of $CaCl_2$ as a mixture of di- and trihydrate in 20 parts of water was then rapidly added with mixing to produce a yellow cake of insolubilized matrix. The amount of $CaCl_2$ added provided a $Ca^{++}:Na^+$ molar ratio of approximately 1:2. After squeezing out the residual water, the cake was dried to yield 51 parts of encapsulated product containing 2.5% core material.

EXAMPLE 3

The procedure of Example 2 was repeated using 20 parts trifluralin herbicide to yield 70 parts of encapsulated product containing 28.5% core material.

Although trifluralin is very soluble in organic solvents such as hexane and acetone, these solvents were unable to extract substantial amounts of core material from the encapsulated product. Ten parts of encapsulated product in 50 parts of hexane was allowed to stand at ambient temperature for 30 minutes. Analysis of the product revealed that only 5% of the trifluralin was extracted into the hexane.

EXAMPLES 4–12

On a dry weight basis, 40 parts of unmodified pearl corn starch was suspended in 250 parts of water and was gelatinized at room temperature by the addition of sodium hydroxide in a sufficient amount of water such that the sodium starchate paste had an equivalent starch concentration of approximately 10.9%. A melt of 20.0 parts trifluralin herbicide was dispersed in the paste which was then insolubilized with an aqueous solution of $CaCl_2$ as a mixture of the di- and trihydrates. The resultant cake was dewatered, dried, and analyzed for trifluralin content. The percent active ingredient encapsulated varied with the proportions of starch, sodium hydroxide, and calcium chloride as reported below in Table I.

EXAMPLE 13

On a dry weight basis, 40 parts of acid-modified sorghum flour was suspended in enough water to give a 40% solids concentration and was then treated with 5 parts of sodium hydroxide to gelatinize the starch. The molar ratio of NaOH:starch AGU was 1:2. A melt of 5 parts of trifluralin herbicide was dispersed in the paste which was then insolubilized by rapidly stirring in 10 parts of $CaCl_2$ as a mixture of di- and trihydrate constituting a $Ca^{++}:Na^+$ molar ratio of approximately 1:2. The isolated product was analyzed to yield 90% trifluralin recovery, of which 61% was encapsulated.

TABLE I

| Example | Parts NaOH | Approximate molar ratio NaOH:starch AGU | Parts $CaCl_2$ hydrate | Approximate molar ratio $Ca^{++}:Na^+$ | Trifluralin encapsulated (%) |
|---|---|---|---|---|---|
| 4 | 5 | 1:2 | 10 | 1:2 | 94 |
| 5 | 5 | 1:2 | 20 | 1:1 | 85 |
| 6 | 5 | 1:2 | 30 | 1:0.66 | 80 |
| 7 | 10 | 1:1 | 18 | 1:2.2 | 66 |
| 8 | 10 | 1:1 | 20 | 1:2 | 69 |
| 9 | 10 | 1:1 | 22 | 1:1.8 | 48 |
| 10 | 15 | 3:2 | 26 | 1:2.3 | 75 |
| 11 | 15 | 3:2 | 30 | 1:2 | 61 |
| 12 | 15 | 3:2 | 34 | 1:1.7 | 59 |

EXAMPLE 14

The procedure of Example 13 was repeated except that acid-modified starch was substituted for the flour. The recovery was 92%, of which 66% was found to be encapsulated.

EXAMPLE 15

On a dry weight basis, 40.5 parts of unmodified pearl corn starch was suspended in a dispersion of 250 parts of water and 11.5 parts of the insecticide fonofos (O-ethyl-S-phenyl ethylphosphorodithioate). The starch was gelatinized at room temperature with 5 parts sodium hydroxide dissolved in 75 parts water. The molar ratio of NaOH:starch AGU was 1:2. Ten parts of $CaCl_2$ as a mixture of di- and trihydrate constituting a $Ca^{++}:Na^+$ molar ratio of approximately 1:2 in 20 parts water was then rapidly added with mixing to produce an insolubilized matrix. The product was isolated and dried to yield 61 parts of encapsulated material containing 4.14% sulfur and 15.9% core material.

EXAMPLE 16

The procedure of Example 15 was repeated except the herbicide EPTC (S-ethyl dipropylcarbamothioate) was substituted for the fonofos and insolubilization was effected with an aqueous mixture of 9 parts $CaCl_2.2H_2O$ and 1 part $CuCl_2.H_2O$. The copper salt was added to slow the potential breakdown of the starch in soil. The product was isolated and dried to yield 65 parts of encapsulated material containing 1.2% nitrogen and 16% core material.

Although EPTC is a volatile herbicide, a sample of the product did not lose any measurable amount of EPTC after standing in an open flask for 3 months. Another sample lost 18% EPTC after standing under wet conditions for 4 days. In comparison, nonencapsulated product lost 90% of its EPTC after standing 1 day under wet conditions.

EXAMPLE 17

Twelve parts of the insecticide DDT [1,1'-(2,2,2-trichloroethylidene) bis(4-chlorobenzene)] dissolved in 25 parts acetone was dispersed in 370 parts of the sodium starchate prepared in Example 1(B). Ten parts of $CaCl_2$ as a mixture of di- and trihydrate constituting a $Ca^{++}$:$Na^{+}$ molar ratio of approximately 1:2 in 20 parts water was then rapidly added with mixing to produce an insolubilized matrix. The product was isolated and dried as in Example 2 to yield 58 parts of encapsulated product containing 9.6% chlorine and 19.2% core material.

A 10-g. test sample of the product was extracted three times with 25-ml. portions of acetone, and retained 59.3% of the DDT.

EXAMPLE 18

Ten parts of EPTC was dispersed in 375 parts of the sodium starchate solution prepared in Example 1(A). Ten parts of $CaCl_2.2H_2O$ in 20 parts of water was then rapidly added with mixing to produce an insolubilized matrix. The product was isolated and dried as in Example 2 to yield 65 parts of encapsulated product containing 0.83% nitrogen and 11% core material.

EXAMPLES 19–23

In order to compare the relative effectiveness of calcium, barium, and strontium adducts of starch as encapsulating agents, Example 3 was repeated employing various amounts of the chloride salts of the respective cations as reported in Table II. The percent trifluralin encapsulated is expressed as the percent of the amount initially added.

It is understood that the foregoing detailed description is given merely by way of illustration and that modification and variations may be made therein without departing from the spirit and scope of the invention.

TABLE II

| Example | Insolubilizing agent | Approximate molar ratio of cation to $Na^+$ | Trifluralin encapsulated (%) |
|---|---|---|---|
| 19 | $CaCl_2.2H_2O$ | 1:2 | 95.0 |
| 20 | $CaCl_2.2H_2O$ | 1:1 | 85.5 |
| 21 | $SrCl_2.6H_2O$ | 1:2 | 70.5 |
| 22 | $SrCl_2.6H_2O$ | 1:1 | 88.5 |
| 23 | $BaCl_2.2H_2O$ | 1:2 | 87.0 |

I claim:

1. A method of encapsulating a water-insoluble, chemical biological agent comprising the steps of:

a. preparing a dispersion of a suitable chemical biological agent in a matrix-forming material comprising an aqueous paste of a starchcontaining material (SCM) alkoxide, wherein said paste has a solids concentration of SCM alkoxide of from about 6–20%, and wherein the relative amount of said SCM alkoxide with respect to said biological agent is sufficient to entrap said agent within a matrix of said SCM;

b. reacting from a single phase said SCM alkoxide with a suitable bivalent cation selected from the group consisting of calcium, barium, and strontium to form a continuous insolubilized matrix having entrapped therein discontinuous domains of said agent; and c. recovering said entrapped chemical biological agent.

2. A method as described in claim 1 wherein the suitable chemical biological agent is a water-insoluble herbicide, insecticide, fungicide, nematocide, bactericide, rodenticide, molluscide, acaricide, larvacide, fumigant, animal repellant, insect repellant, plant growth regulator, fertilizer, pheromone, sex lure, flavor composition, or odor composition.

3. A method as described in claim 1 wherein the suitable chemical biological agent is S-ethyl dipropylcarbamothioate, S-propyl dipropylcarbamothioate, S-propyl butylethylcarbamothioate, S-ethyl cyclohexylethylcarbamothioate, S-ethyl bis(2-methylpropyl)-carbamothioate, S-ethyl hexahydro-1-H-azepine-1-carbothioate, S-(2,3,3-trichloro-2-propenyl)bis(1-methylethyl)carbamothioate, 2,6-dinitro-N,N-dipropyl-4-(trifluoromethyl)benzenamine, N-butyl-N-ethyl-2,6-dinitro-4-(trifluoromethyl) benzenamine, N-(cyclopropylmethyl)-2,6-dinitro-N-propyl-4-(trifluoromethyl) benzenamine, 2-chloro-N-(2-ethyl-6-methylphenyl)-N-(2-methoxy-1-methylethyl) acetamide, 2-chloro-N-(2,6-diethylphenyl)-N-(methoxymethyl) acetamide, 2,4-dichlorophenoxyacetic acid, propylene glycol butyl ether, 2,6-dichlorobenzonitrile, 3a,4,7,7a-tetrahydro-2-[(trichloromethyl)thio]-1-H-isoindole-1,3(2H)-dione, 3a,4,7,7a-tetrahydro-2-[(1,1,2,2-tetrachloroethyl) thio]-1-H-isoindole-1,3(2H)-dione, N-[[(4-chlorophenyl) amino] carbonyl]-2,6-difluorobenzamide, 1,1'-(2,2,2-trichloroethylidene) bis(4-chlorobenzene), O,O-diethyl O-6-methyl-2-(1-methylethyl)-4-pyrimidinyl phosphorothioate, O-ethyl-S-phenyl ethylphosphorodithioate, or 1,2-dibromo-3-chloropropane.

4. A method as described in claim 1 wherein said SCM alkoxide is the sodium or potassium salt of cereal starch, potato starch, cereal flour, or potato flour.

5. A method as described in claim 1 wherein said SCM alkoxide is the sodium or potassium salt of acid-modified starch.

6. A method as described in claim 1 wherein said bivalent cation is calcium.

7. A composition of matter produced by the process of claim 1.

8. A composition of matter produced by the process of claim 2.

9. A composition of matter produced by the process of claim 3.

10. A composition of matter produced by the process of claim 4.

11. A composition of matter produced by the process of claim 6.

* * * * *